(12) United States Patent
Markworth et al.

(10) Patent No.: US 7,789,899 B2
(45) Date of Patent: Sep. 7, 2010

(54) BONE ANCHORAGE SCREW WITH BUILT-IN HINGED PLATE

(75) Inventors: Aaron D. Markworth, Mountain View, CA (US); Hugues F. Malandain, Mountain View, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1121 days.

(21) Appl. No.: 11/027,500

(22) Filed: Dec. 30, 2004

(65) Prior Publication Data
US 2006/0149252 A1    Jul. 6, 2006

(51) Int. Cl.
*A61B 17/80* (2006.01)
(52) U.S. Cl. ..................................... 606/286
(58) Field of Classification Search ............... 606/286, 606/287, 71, 900, 264
See application file for complete search history.

(56) References Cited

U.S. PATENT DOCUMENTS

| | | | |
|---|---|---|---|
| 2,486,303 A * | 10/1949 | Longfellow | 606/71 |
| 3,779,240 A | 12/1973 | Kondo | |
| 4,493,317 A | 1/1985 | Klaue | |
| 4,763,644 A | 8/1988 | Webb | |
| 4,805,602 A | 2/1989 | Puno et al. | |
| 4,946,458 A | 8/1990 | Harms et al. | |
| 5,005,562 A | 4/1991 | Cotrel | |
| 5,053,036 A | 10/1991 | Perren et al. | |
| 5,057,111 A | 10/1991 | Park | |
| 5,127,912 A * | 7/1992 | Ray et al. | 606/250 |
| 5,129,388 A | 7/1992 | Vignaud et al. | |
| 5,129,899 A | 7/1992 | Small et al. | |
| 5,147,361 A | 9/1992 | Ojima et al. | |
| 5,151,103 A | 9/1992 | Tepic et al. | |
| 5,171,279 A | 12/1992 | Mathews | |
| 5,176,678 A | 1/1993 | Tsou | |
| 5,176,679 A | 1/1993 | Lin | |
| 5,180,381 A | 1/1993 | Aust et al. | |
| 5,207,678 A | 5/1993 | Harms et al. | |
| 5,234,431 A | 8/1993 | Keller | |
| 5,246,442 A | 9/1993 | Ashman et al. | |
| 5,253,406 A | 10/1993 | Shere et al. | |
| 5,261,909 A | 11/1993 | Sutterlin et al. | |
| 5,269,784 A | 12/1993 | Mast | |
| 5,290,288 A | 3/1994 | Vignaud et al. | |
| 5,324,290 A | 6/1994 | Zdeblick et al. | |
| 5,360,431 A | 11/1994 | Puno et al. | |

(Continued)

FOREIGN PATENT DOCUMENTS

DE    94 02 695 U1    4/1994

(Continued)

*Primary Examiner*—Thomas C Barrett
*Assistant Examiner*—Michael J Araj (57) ABSTRACT

An implantable medical device and methods of use thereof are provided for supporting a structure. The structure supported can include a bony structure. The device is comprised of a screw assembly including a base and a support configured for receiving one or more anchor assemblies. The support includes a top portion, a bottom portion and an interconnection means for coupling the base to the support. The interconnection means allows the support to be positionable in a first position that is substantially parallel to a long axis of the base and secondarily positionable substantially perpendicular to the long axis of the base. The base and the one or more anchor assemblies are configured for attachment to a structure in a patient.

20 Claims, 7 Drawing Sheets

U.S. PATENT DOCUMENTS

| | | |
|---|---|---|
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,466,238 A | 11/1995 | Lin |
| 5,474,551 A | 12/1995 | Finn et al. |
| 5,474,555 A | 12/1995 | Puno et al. |
| 5,476,464 A | 12/1995 | Metz-Stavenhagen et al. |
| 5,478,801 A | 12/1995 | Lang et al. |
| 5,480,401 A | 1/1996 | Navas |
| 5,480,440 A | 1/1996 | Kambin |
| 5,499,983 A | 3/1996 | Hughes |
| 5,501,684 A | 3/1996 | Schlapfer et al. |
| 5,520,690 A | 5/1996 | Errico et al. |
| 5,531,746 A | 7/1996 | Errico et al. |
| 5,549,608 A | 8/1996 | Errico et al. |
| 5,554,157 A | 9/1996 | Errico et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,607,426 A | 3/1997 | Ralph et al. |
| 5,609,593 A | 3/1997 | Errico et al. |
| 5,647,873 A | 7/1997 | Errico et al. |
| 5,649,926 A | 7/1997 | Howland et al. |
| 5,669,911 A | 9/1997 | Errico et al. |
| 5,672,176 A | 9/1997 | Biedermann et al. |
| 5,733,285 A | 3/1998 | Errico et al. |
| 5,733,286 A | 3/1998 | Errico et al. |
| 5,817,094 A | 10/1998 | Errico et al. |
| 5,876,403 A | 3/1999 | Shitoto et al. |
| 5,882,350 A | 3/1999 | Ralph et al. |
| 5,885,286 A | 3/1999 | Sherman et al. |
| 5,951,553 A | 9/1999 | Betz et al. |
| 5,964,761 A | 10/1999 | Kambin |
| 5,964,988 A | 10/1999 | LaRose et al. |
| 6,007,536 A * | 12/1999 | Yue .......................... 606/60 |
| 6,022,350 A | 2/2000 | Ganem |
| 6,030,389 A | 2/2000 | Wagner et al. |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,113,601 A | 9/2000 | Tatar |
| 6,280,442 B1 | 8/2001 | Barker et al. |
| 6,296,644 B1 | 10/2001 | Saurat et al. |
| 6,315,779 B1 | 11/2001 | Morrison et al. |
| 6,355,036 B1 * | 3/2002 | Nakajima .................... 606/57 |
| 6,585,738 B1 | 7/2003 | Mangione et al. |
| 6,620,164 B2 * | 9/2003 | Ueyama et al. ............. 606/261 |
| 6,682,530 B2 | 1/2004 | Dixon et al. |
| 6,736,817 B2 | 5/2004 | Troxell et al. |
| 6,744,829 B1 | 6/2004 | Bono et al. |
| 6,858,031 B2 | 2/2005 | Morrison et al. |
| 6,884,241 B2 | 4/2005 | Bertranou et al. |
| 6,887,241 B1 | 5/2005 | McBride et al. |
| 7,220,262 B1 | 5/2007 | Hynes |
| 7,524,323 B2 | 4/2009 | Malandain |
| 2002/0007183 A1 | 1/2002 | Lee et al. |
| 2002/0026194 A1 | 2/2002 | Morrison et al. |
| 2002/0143338 A1 * | 10/2002 | Orbay et al. .................. 606/69 |
| 2003/0032957 A1 | 2/2003 | McKinley et al. |
| 2003/0105460 A1 | 6/2003 | Crandall et al. |
| 2003/0114853 A1 | 6/2003 | Burgess et al. |
| 2003/0135210 A1 | 7/2003 | Dixon et al. |
| 2004/0054371 A1 | 3/2004 | Dierks et al. |
| 2004/0087949 A1 | 5/2004 | Bono et al. |
| 2004/0092931 A1 | 5/2004 | Taylor et al. |
| 2004/0102778 A1 * | 5/2004 | Huebner et al. .............. 606/71 |
| 2004/0127897 A1 | 7/2004 | Freid et al. |
| 2004/0153070 A1 * | 8/2004 | Barker et al. ................. 606/61 |
| 2004/0167521 A1 * | 8/2004 | De Windt .................... 606/69 |
| 2004/0225290 A1 | 11/2004 | Ferree |
| 2005/0038434 A1 | 2/2005 | Mathews |
| 2005/0049588 A1 | 3/2005 | Jackson |
| 2005/0049593 A1 | 3/2005 | Duong et al. |
| 2005/0085812 A1 * | 4/2005 | Sherman et al. .............. 606/61 |
| 2005/0101954 A1 | 5/2005 | Simonson |
| 2005/0113927 A1 | 5/2005 | Malek |
| 2005/0215999 A1 | 9/2005 | Birkmeyer et al. |
| 2005/0216005 A1 * | 9/2005 | Howland ..................... 606/61 |
| 2005/0228376 A1 * | 10/2005 | Boomer et al. ............... 606/61 |
| 2005/0234451 A1 | 10/2005 | Markworth |
| 2005/0234452 A1 | 10/2005 | Malandain |
| 2005/0234456 A1 | 10/2005 | Malandain |
| 2006/0149237 A1 | 7/2006 | Markworth et al. |

FOREIGN PATENT DOCUMENTS

| | | |
|---|---|---|
| DE | 94 02 695.5 U1 | 5/1994 |
| WO | WO 00/54681 A2 | 9/2000 |
| WO | 02/076315 | 10/2002 |
| WO | 2004/064603 | 8/2004 |
| WO | 2004/093701 | 11/2004 |

* cited by examiner

BONE ANCHORAGE SCREW WITH BUILT-IN HINGED PLATE

TECHNICAL FIELD

This invention relates to medical devices.

BACKGROUND

The use of spinal stabilization/fixation devices to align or position specific vertebrae or a region of the spine is well established. Typically such devices utilize a spinal fixation element, comprised of a relatively rigid member such as a plate, board or rod that is used as a coupler between adjacent vertebrae. Such a spinal fixation element can effect a rigid positioning of adjacent vertebrae when attached to the pedicle portion of the vertebrae using pedicle bone anchorage screws. Once the coupled vertebrae are spatially fixed in position, procedures can be performed, healing can proceed or spinal fusion may take place.

Spinal fixation elements may be introduced posteriorly to stabilize the various vertebrae of the spine, for example, in conjunction with a kyphoplasty procedure wherein a void or cavity is made inside a vertebral body followed by filling with a bone substitute to form an "internal cast." Some conventional devices for this purpose are designed to be attached directly to the posterior of the spine, but the generally invasive nature of a conventional posterior approach used to implant these devices poses drawbacks. One minimally invasive solution to the problem of the posterior approach involves making a longitudinal separation of the sacrospinalis group between the multifudus and longissimus utilizing the natural cleavage plane between these two muscles rather than detaching the paraspinal muscles from the posterior spinal elements. Problems stemming from the prior art solutions include a high degree of invasiveness resulting in muscle disruption and blood loss. The loss of the paraspinal muscle attachment sites, formation of scar tissue, and loss of muscle function may compromise the patient's final outcome. Additionally, the prior art solutions are time consuming and are difficult to remove.

SUMMARY

In general, in one aspect, the invention features a medical device for supporting a structure comprising a screw assembly. The screw assembly includes a base and a support configured for receiving one or more anchor assemblies. The support includes a top portion and a bottom portion, and an interconnection means for coupling the base to the support. The interconnection means allows the support to be positionable in a first position that is substantially parallel to a long axis of the base and secondarily positionable substantially perpendicular to the long axis of the base. The base and the one or more anchor assemblies are configured for attachment to a structure in a patient.

Implementations of the invention can include one or more of the flowing features. The structure supported by the device can be bone selected from the group including a vertebra, femur, tibia, fibula, humerus, radius, ulna, calcaneous, and a pelvis.

The screw assembly of the device can have an overall length sized for subcutaneous support of the posterior of a spine. The base of the screw assembly can be comprised of a base head having a shape and a locking means and an anchor. The base head shape can be an open saddle-type head. The locking means of the base can be comprised of a setscrew, wherein the setscrew is configured to link the support and the base, and wherein tightening the setscrew effects locking of the support in a position relative to a long axis of the base. The anchor of the base can be selected from the group including a screw, staple, nail, hook and a pin. In one embodiment, the anchor is a screw configured for bone anchoring. In another embodiment, the anchor is a screw configured for insertion into the pedicle of a vertebra.

The support of the device can have a shape selected from the group including a board, plate, elongated cross-section, oval, square, I-beam and a rod. The support can include a connector end, one or more apertures, and a receiver. The connector end can be configured for interconnection of the support and the base of the screw assembly. In one embodiment, the connector end is configured for hinge-type interconnection of the support and the base of the screw assembly.

The one or more apertures of the support can include a first connector end proximal aperture having a dimensional configuration to support a range of movement of the base in relation to the support. The apertures can further include one or more second connector end distal apertures for providing access to the base and the means for locking the anchor assembly to the support, when assembled with the support.

The support can include a support member having a top portion and a bottom portion, a head assembly, and an interconnection means. In one embodiment, the support member can include a receiver, and one or more apertures. The one or more apertures include a first aperture wherein an anchor assembly is passable therethrough and lockably engagable with the support member, and a second aperture wherein access is provided from the top portion of the support member to access the head assembly.

The head assembly of the support can include a connector end, an aperture having a dimensional configuration supporting a range of movement of the base in relation to the support, and a connector end proximal aperture having a dimensional configuration to support a range of movement of the base in relation to the support. The head assembly can also include a locking means for securing the head assembly to the support member, wherein the head assembly is configured for interconnection with the support member.

In general in another aspect, the invention features a method of supporting a bony structure, the method including the steps of: 1) delivering to bone a screw assembly comprising a support having a receiver, a base, an interconnection means, and a locking means; 2) deploying the support substantially perpendicular to the long axis of the base; 3) passing through the support and implanting one or more anchor assemblies having a base and a locking means into bone; 4) locking the bases within one or more of the anchor assemblies; 5) locking one or more of the anchor assemblies within the support receiver; and 6) engaging the locking means of the screw assembly to secure the position of the support in relation to the base.

In general in a further aspect, the invention features a method of supporting a bony structure, the method comprising the steps of: 1) delivering to bone a screw assembly including: a support comprising a support member having a receiver, a head assembly having a connector end an interconnection means and a locking means for securing the head assembly to the support member; a base; an interconnection means, and a locking means for securing the support in a position in relation to the base; 2) deploying the support substantially perpendicular to the long axis of the base; 3) passing through the support and implanting one or more anchor assemblies having a base and a locking means into bone; 4) locking the bases within one or more of the anchor assemblies; 5) locking one or more of the anchor assemblies within the support receiver; 6) locking the head assembly within the support member; and engaging the locking means of the screw assembly to secure the position of the support in relation to the base.

Aspects of the invention may include one of the following advantageous features. In various implementations of the invention the support and screw assembly can be pre-loaded together. As such there is no need to connect the support and screw assembly at the surgical site. Use of the invention requires few user manipulations. For example, the screw assembly can first be inserted into the pedicle of a vertebrae. Next, the support which is connected by an interconnection means to the screw assembly can be deployed to a desired position. Subsequently, one or more anchor assemblies can be added to the support for attachment to additional vertebrae.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
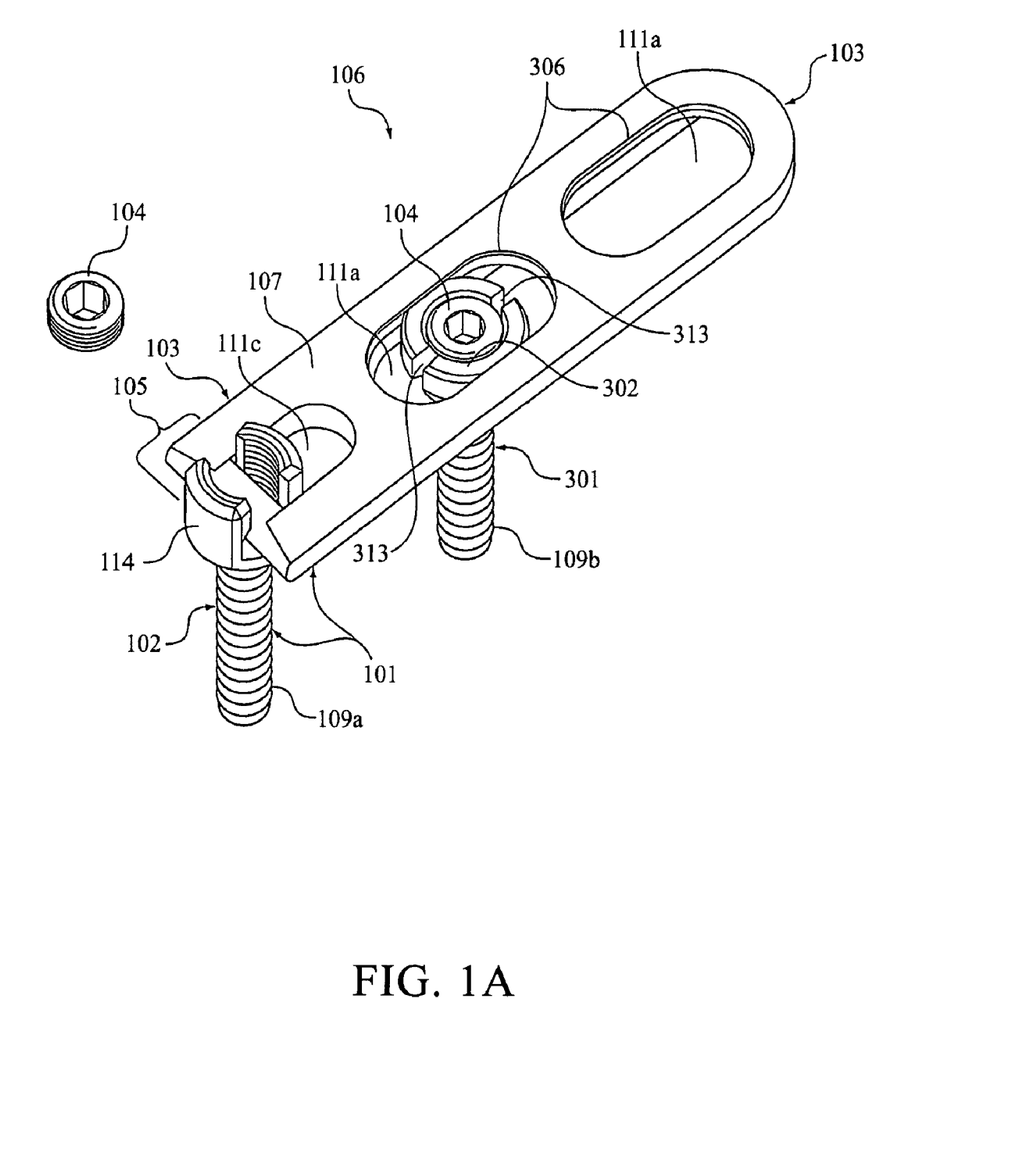
FIG. 1A is a drawing of a support assembly.
Figure 1B:
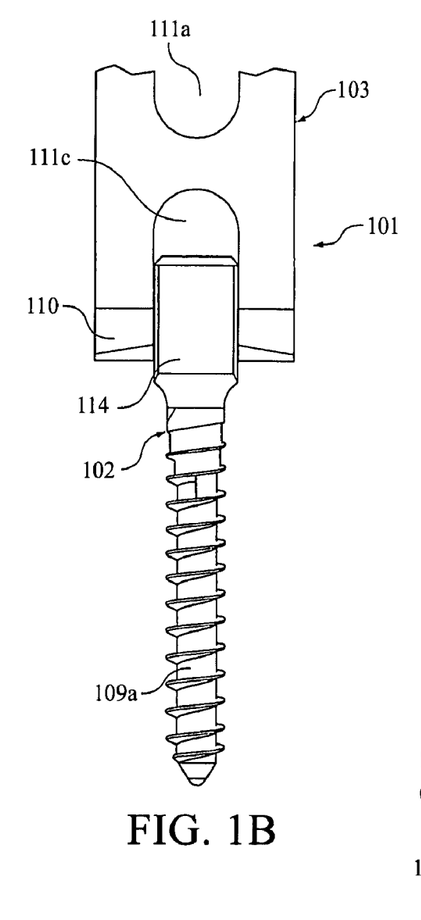
FIGS. 1B-C are drawings of a screw assembly having a base and a support, illustrating the interconnection between the base and the support such that the support is positioned substantially parallel (FIG. 1B) or perpendicular (FIG. 1C) to a long axis of the base.
Figure 1C:
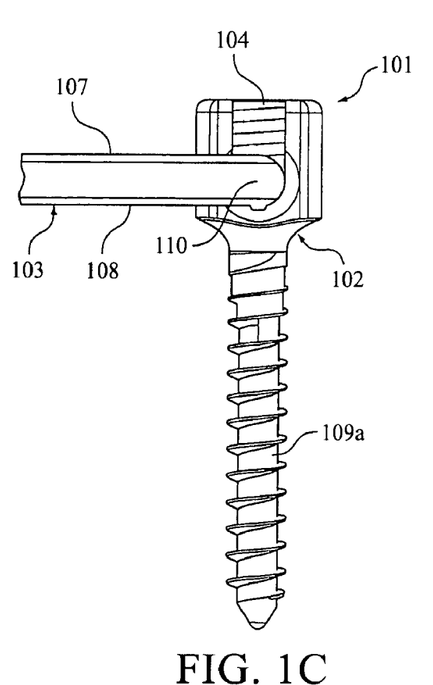
Figure 1D:
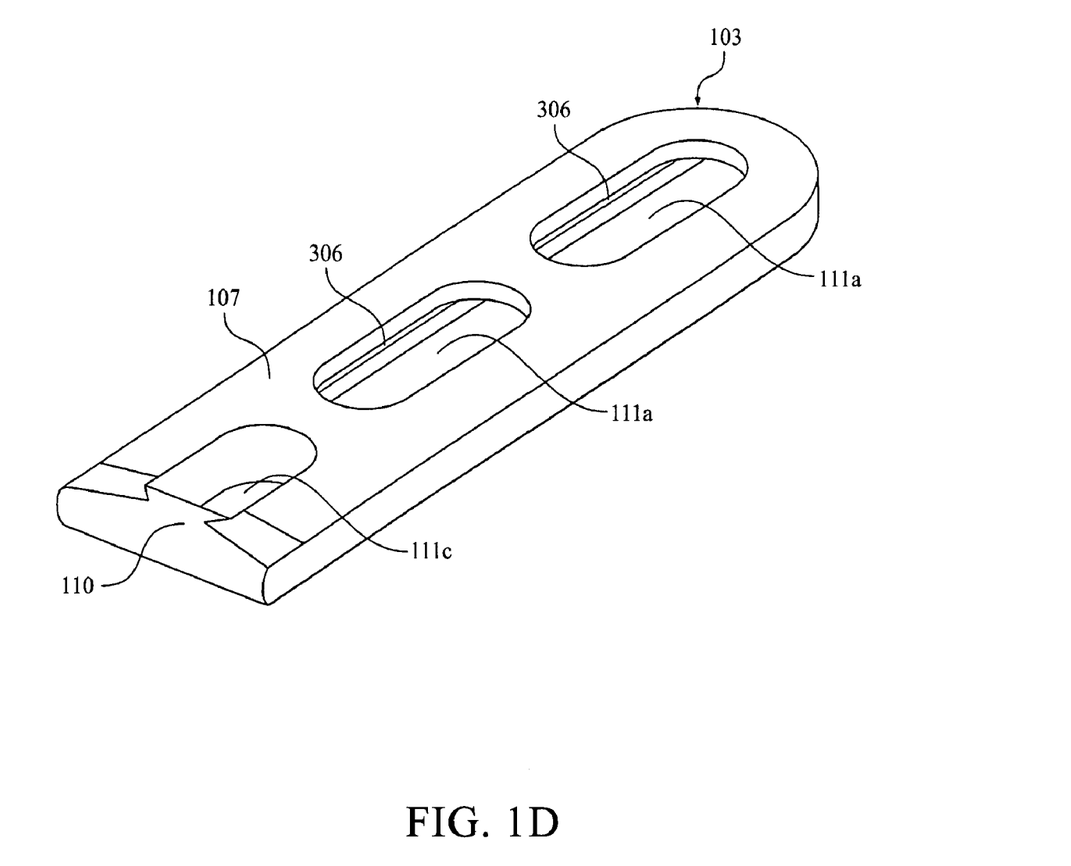
FIG. 1D is a drawing of a support.
Figure 2A:
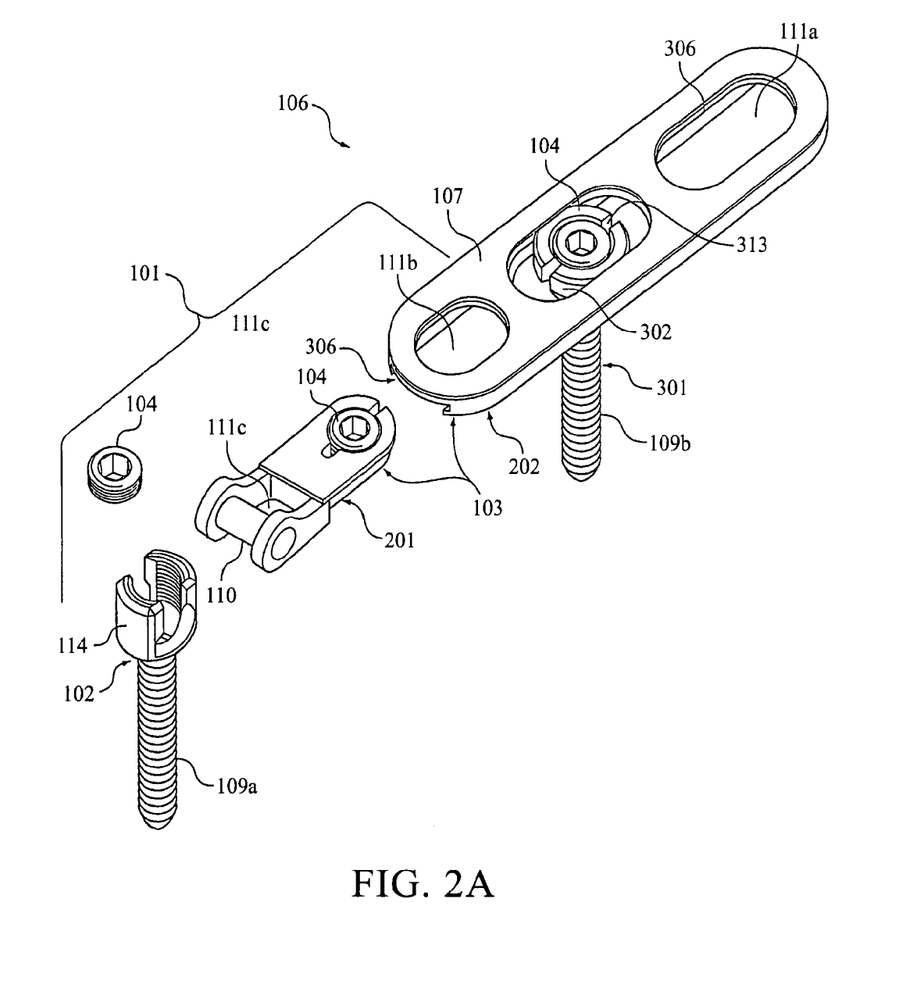
FIG. 2A is a drawing of an alternative support assembly.

As shown in FIGS. 1A and 2A, a screw assembly 101 is provided comprising a base 102, a support 103 configured for receiving one or more anchor assemblies 301 and an interconnection means 105 between the base 102 and the support 103. As shown in FIGS. 1A, 1C, 1D and 2A-2E, the support 103 includes a top portion 107 and a bottom portion 108 (see FIGS. 1B, 1C, 2D and 2E). The interconnection means 105 allows the support 103 to be positionable in a first position that is substantially parallel to a long axis of the base 102 (see FIGS. 1B, 2B-2D) and secondarily deployed or positioned substantially perpendicular to the long axis of the base 102 (see FIGS. 1A, 1C, 2A and 2E). The base 102 of the screw assembly 101 and the one or more anchor assemblies 301 are configured for attachment to a structure (e.g. bone) in a patient. In application, a screw assembly 101 receives one or more anchor assemblies 301 to form a support assembly 106 (see FIGS. 1A and 2A). In one implementation, the anchor assembly 301 is combined with the screw assembly 101 after deployment of the support 103 (forming support assembly 106) and in another implementation, the anchor assembly 301 is pre-assembled with the screw assembly 101. One advantage of the invention over the prior art solutions is timesavings when using the support assembly 106 for supporting a structure. Another advantage is relative ease of removal. The support assembly 106 can be used for temporary or permanent implantation.

The support assembly 106, once assembled, can be used to support a bony structure. The bony structure supported can include a femur or other bones of the leg (e.g. tibia and fibula), bones of the arm and wrist (e.g. humerus, radius and ulna), and other bones such as the calcaneous, pelvis, spine (vertebrae) and the like. Support can be provided for a single bone (i.e. a long bone such as the femur, tibia, humerus) or for more than one bone (i.e. vertebrae).

The screw assembly 101 can be made of materials that are durable and that can be implanted in a body, including titanium, stainless steel, carbon fiber, etc. In one implementation, the screw assembly 101 is made of titanium. In another implementation the screw assembly 101 is made of a biocompatible material, a reabsorbable material or a combination of any of the foregoing materials. The dimensions of the screw assembly 101 vary with the application. In general, the length of the screw assembly 101 is from 20 to 1,000 millimeters. In one implementation, the length is substantially between 50 and 400 millimeters. In another implementation, the screw assembly 101 is sized for applications involving support of the posterior of the spine (not shown).

As shown in FIGS. 1A-1C, 2A-2E and 3A-3B, the base 102 of the screw assembly 101 is comprised of a base head 114 having a shape and a locking means, and an anchor 109a. The shape of the base head 114 can be comprised of any of a number of shapes suitable for receiving or interconnecting with the support 103. In one implementation, the base head 114 shape is an open saddle-type head. As shown in FIGS. 1A, 1C and 2A, in one implementation, the locking means of the base head 114 can be a setscrew 104. The setscrew 104 can be configured to link the support 103 and the base 102 while permitting a freedom of movement between the base 102 and the support 103 (see FIGS. 1A, 2A and 2E). The locking means can effect locking of the support 103 in a position relative to the base 102. In one implementation the setscrew 104 can be tightened to effect locking of the support 103 in a position relative to (for example, the long axis of) the base 102. In an alternative implementation, the locking means of the base head 114 can be a cam (not shown).

As shown in FIGS. 1A-1C, 2A-2E and 3A-3B, the anchor 109a of the screw assembly 101 is can be selected from the group consisting of a screw, staple, nail, hook and pin. In one implementation, the anchor 109a is configured for bone anchoring. In another implementation, the anchor 109a is a screw configured for insertion into the pedicle of a vertebra.

Figure 3A:
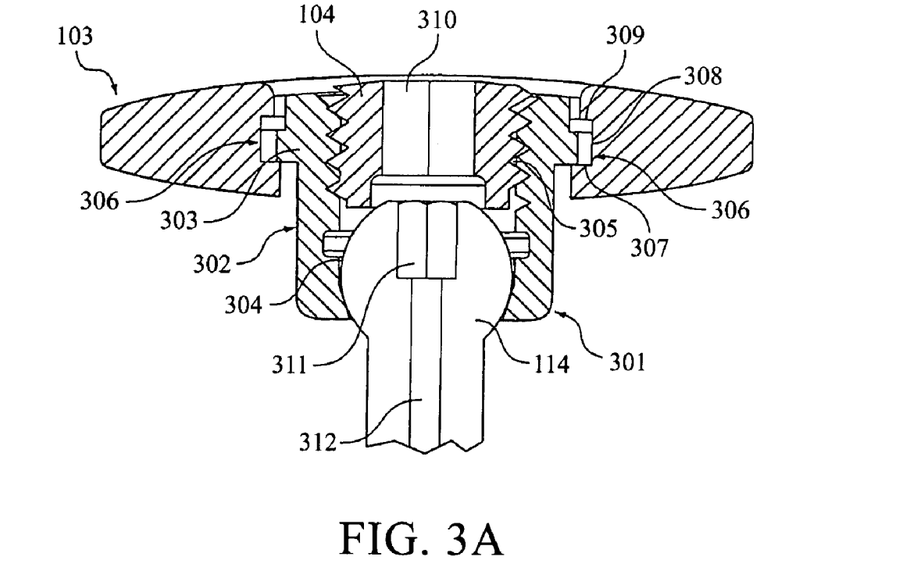
FIG. 3A is a drawing showing a cutaway view of an anchor assembly prior to being secured within the support.
Figure 3B:
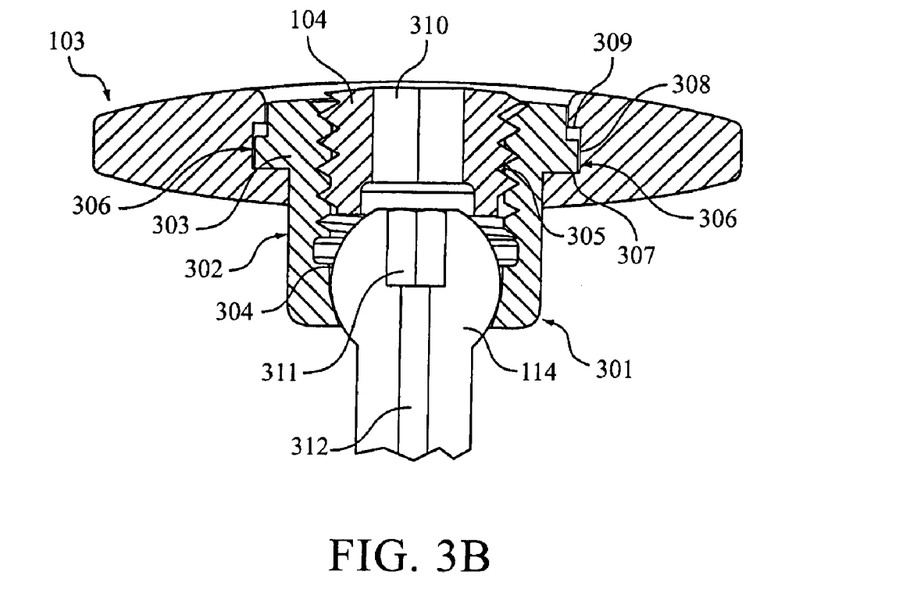
FIG. 3B is a drawing showing a cutaway view of an anchor assembly after being secured within the support.

As shown in FIGS. 1A, 2A and 3A-B, the anchor assembly 301 is configured to interconnect with the shape of the receiver 306 (discussed in detail below). The anchor assembly 301 shape can be any of a number of shapes. In some implementations, the mating between the support 103 and the anchor assembly 301 occurs only in two dimensions (e.g. where a 90 degree twisting receiver 306 is employed). As shown in FIGS. 3A-B, the anchor assembly 301 can be comprised of a head 302, a base 109b and a base head 114. The anchor assembly 301 can be comprised of numerous materials that are durable and that can be implanted in a body, including titanium, stainless steel, carbon fiber, etc. Additionally, the anchor assembly 301 can be comprised of a reabsorbable material or a biocompatible material, or a combination of any of the foregoing materials.

As shown in FIGS. 3A-B, the anchor assembly 301 includes a means for locking the anchor assembly 301 to the support 103. In one implementation, as shown in FIG. 3A, where the receiver 306 and complimentary head 302 of the anchor assembly 301 are T-slot shaped, the means for locking the anchor assembly 301 can be a setscrew 104 threaded into the head 302 of the anchor assembly 301, wherein the head 302 includes a threaded base aperture 305 and a deformable geometry. Such a means for locking an anchor assembly 301 to the support 103 is disclosed in the commonly owned non-provisional patent application Ser. No. 11/019,918 filed Dec. 20, 2004, which is incorporated herein by reference in its entirety. As shown in FIG. 3B, when the setscrew 104 is turned into the threaded base aperture 305, the deformable head 303 is caused to splay outward such that the T-slot shape of the head 302 engages and locks against the receiver 306 planar medial face 308. As shown in FIGS. 3A and 3B, the setscrew 104 can be disposed such that it is constrained within the threaded base aperture 305. The constrained setscrew 104 upon final tightening can be over-constrained thereby forcing the deformable head 303 to splay outward. In another implementation, the head 302 may additionally engage the receiver 306 planar upper face 309 or planar lower face 307 or both to effect locking. In another implementation, a cam can be substituted for the setscrew 104 to effect the locking of the anchor assembly 301 within the support 103 (not shown).

The deformable geometry of the deformable threaded base aperture 305 can be comprised of a void within the anchor assembly 301 head 302 wherein the void is selected from the list consisting of a cavity, slot notch, groove, cut out, gap and a recess. In one implementation, the void is tapered. In another implementation as shown in FIGS. 1A and 2A, the void within the anchor assembly 301 head 302, can be a slot 313 cut into the head 302.

Other means for locking an anchor assembly 301 to the support 103 are possible, including those disclosed in U.S. application Ser. No. 10/826,684, filed Apr. 16, 2004, entitled "Subcutaneous Support", which is incorporated herein by reference in its entirety.

As shown in FIGS. 3A-B, the anchor assembly 301 includes a base 102 moveably disposed within the threaded base aperture 305. The base 102 can be a screw, staple, hook or nail and of a type typically used for anchoring to a structure (e.g., to a bone). In one implementation, the base 102 is a screw of a type for insertion into the pedicle of a vertebra. In another implementation, the base 102 can be attached to another bony structure.

Attachment of the base 102 to the anchor assembly 301 can be accomplished in numerous ways. In one implementation, the attachment is through a hinge-type of connection between the base 102 and the anchor assembly 301 (not shown). Such a means for connecting the base 102 and the anchor assembly 301 is disclosed in U.S. application Ser. No. 10/825,962, filed Apr. 16, 2004, which is incorporated herein by reference in its entirety. In another implementation, as shown in FIGS. 3A-B, the attachment is made between a polyaxial-type base head 114 on the base 102 and a complimentary receptacle 304 within the anchor assembly 301 head 302.

The anchor assembly 301 further includes a means for locking the base 102 within the anchor assembly 301 head 302. As shown in FIGS. 3A-B, for a polyaxial-type base head 114, the means for locking can include a setscrew 104 disposed within a threaded base aperture 305. In this configuration, turning the setscrew 104 causes the setscrew 104 to press directly against the polyaxial base head 114 of the base 102, thereby forcing it against the receptacle 304 of the anchor assembly 301 to effect locking. Alternatively, where the base 102 is of the hinge-type, the means for locking can be comprised of a setscrew 104 disposed in a threaded base aperture 305. In this configuration, turning the setscrew 104 causes the setscrew 104 to press directly against the base head 114 of the hinge-type base 102, thereby creating friction against the hinge's pin to effect locking (not shown). In another implementation, a cam can be substituted for the setscrew 104 to effect locking.

As shown in FIGS. 3A-B, another implementation of the anchor assembly 301 includes a longitudinal aperture 312 through the base 102 and base head 114, a tool interface 311 and a setscrew aperture 310. The longitudinal aperture 312 and setscrew aperture 310 are configured such that an instrument, wire (e.g. a K-wire) or other guide can pass through the entire anchor assembly 301. The setscrew aperture 310 is further configured such that a tool or instrument can pass through the setscrew aperture 310 to engage the tool interface 311 of the base 102. Alternatively, the setscrew 104 can be a cam (not shown).

The setscrew aperture 310 can be any shape and can be sized to accommodate the through passage and use of objects and tools without affecting the positioning of the setscrew 104.

The longitudinal aperture 312 can have any desired cross-sectional shape including but not limited to round, square, hexagonal, oval or any regular or irregular shape.

The tool interface 311 can be any shape suitable for receiving a tool for manipulating the base 102. For example, where the base 102 is a screw, the tool interface 311 can be a hex shape, or any other commonly used screw head tool interface shape.

Where an anchor assembly 301 is configured as shown in FIGS. 3A-B, the setscrew 104 can be pre-positioned within the base aperture 305 without being tightened. The setscrew aperture 310 and longitudinal aperture 312 (passing through the base 102 and base head 114) enable access through a pre-assembled implementation of the anchor assembly 301. Additionally, wherein the anchor assembly 301 is pre-assembled, access is provided to the tool interface 311 of the base head 114 through the setscrew aperture 310.

As shown in FIGS. 1A, 1D, 2A, 2D and 2E, the support 103 has a shape. The shape of the support 103 can be selected from the group consisting of a board, plate, elongated cross-section, oval, square, I-beam and a rod. In one implementation, as shown in FIGS. 1A, 1D, 2A, 2D and 2E, the support is shaped as a plate. In one implementation, the length of the support 103 is minimally substantially the same length as required to span two or more vertebrae. In one implementation, the support 103 is substantially a length as required to span three vertebrae. In another implementation, the length of the support 103 is substantially between 25 to 140 millimeters.

As shown in FIGS. 1A-1D, in one implementation the support 103 is comprised of a connector end 110, one or more apertures 111, and a receiver 306. The connector end 110 is configured for interconnection of the support 103 and the base 102 of the screw assembly 101. In one implementation, the connector end 110 is configured for hinge-type interconnection of the support 103 and the base 102 of the screw assembly 101.

As shown in FIGS. 1A, 1B, and 1D, in one implementation the one or more apertures 111, of the support 103 include a first aperture 111c positioned proximal to the connector end 110, and a second aperture 111a positioned distal to the connector end 110, in relation to the support 103. As shown in FIGS. 1A, 1B and 1D, the first aperture 111c, can provide for a range of movement for the base 102 in relation to the support 103. In one implementation, the movement of the base 102 in relation to the support 103 includes a hinge-type of movement (see FIGS. 1A-1C). As shown in FIG. 1A, the second aperture 111a can provide for access to the support 103 and the means for locking the anchor assembly 301 to the support 103, when the anchor assembly 301 is assembled with the support 103. In one implementation, the second aperture 111*a* can provide for access to the support 103 from above after the support 103 is deployed into a position that is substantially perpendicular to the base 102.

As shown in FIGS. 1A and 1D, in one implementation, the receiver 306 is disposed within a long axis of the support 103. In another implementation, the receiver 306 is connected to the top portion 107 or the bottom portion 108 of the support 103. In an additional implementation, the receiver 306 substantially spans the length of the support 103. The configuration of the receiver 306 can be comprised of any of a number of designs and shapes. In one implementation, the receiver 306 has a configuration selected from the group consisting of a slot, groove, track, dovetail and a snap-in configuration. In another implementation, the receiver 306 has a 90-degree twist-in configuration. In yet another implementation, the receiver 306 and the anchor assembly 301 are both configured in an interconnecting geometry comprising a T-slot (see FIGS. 3A and 3B). As shown in FIGS. 3A and 3B, in one implementation, the T-slot configuration of the receiver 306 can be comprised of a planar upper face 309, a planar lower face 307 and a planar medial face 308. The receiver 306 can include two ends wherein one or both ends are open or closed (not shown).

Figure 2B:
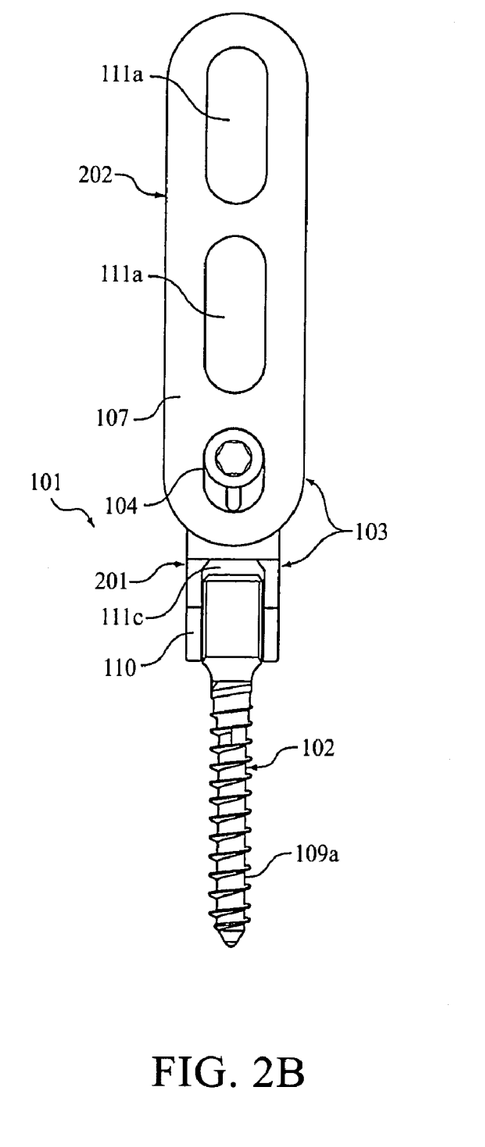
FIGS. 2B-2E are drawings of a screw assembly.
Figure 2C:
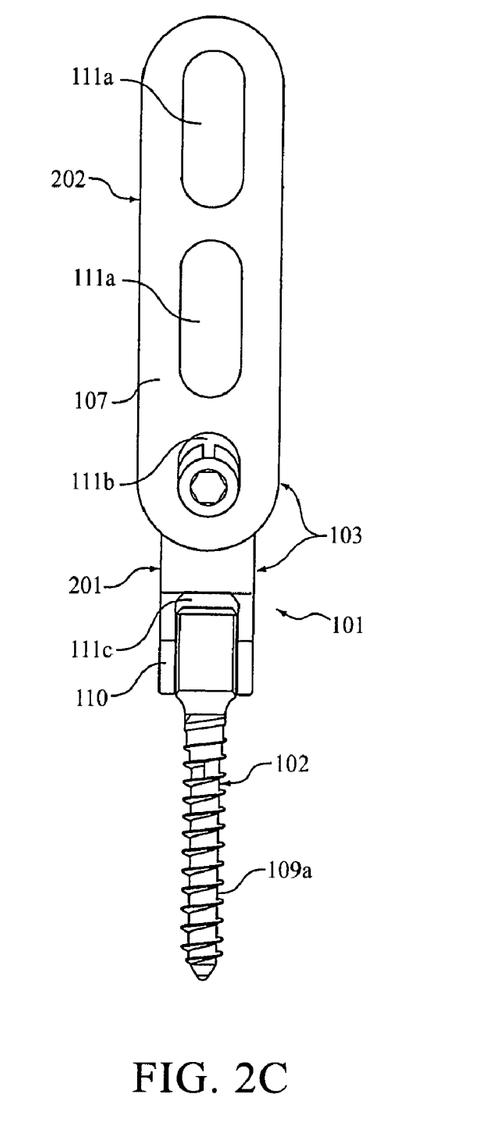
Figure 2D:
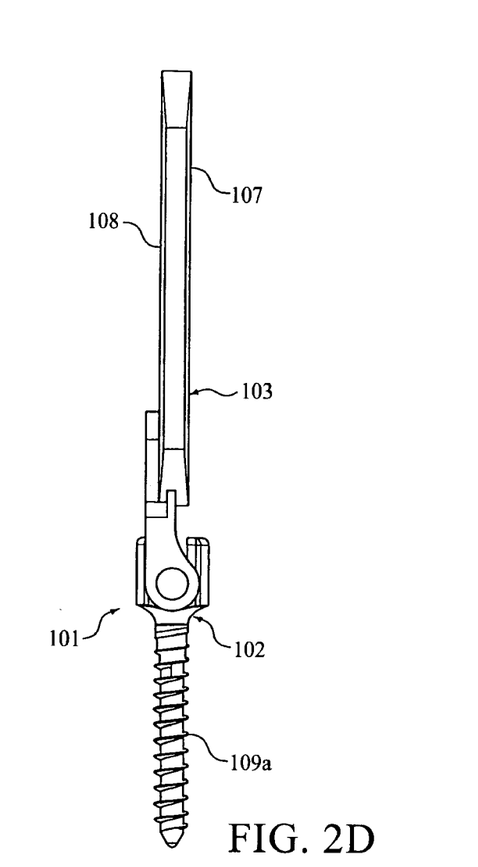
Figure 2E:
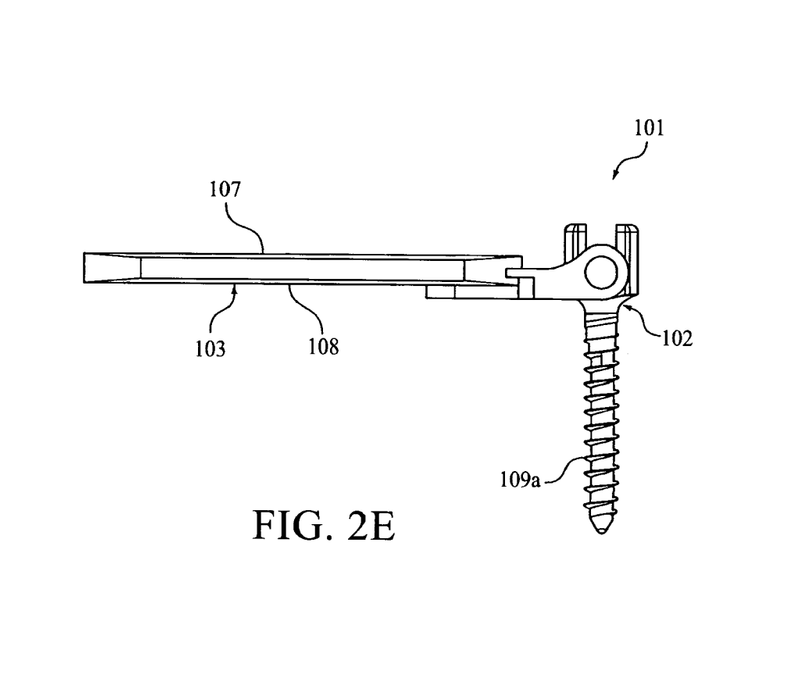

As shown in FIGS. 2A-2E, in one implementation the support 103 is comprised of a support member 202, a head assembly 201 and an interconnection means 105 (for example, a slot-flange combination). The support member 202 can include a top portion 107 and a bottom portion 108 and one or more apertures 111 (see FIGS. 2A-2E). As shown in FIGS. 2A-2C, in one implementation the support member 202 includes a receiver 306 and one or more apertures 111.

As shown in FIG. 2A, in one implementation, the receiver 306 is disposed within a long axis of the support member 202. In another implementation, the receiver 306 is connected to the top portion 107 or the bottom portion 108 of the support member 202 (for example, as an attachment). In an additional implementation, the receiver 306 substantially spans the length of the support member 202. The configuration of the receiver 306 can be comprised of any of a number of designs and shapes. In one implementation, the receiver 306 has a configuration selected from the group consisting of a slot, groove, track, dovetail and a snap-in configuration. In another implementation, the receiver 306 has a 90-degree twist-in configuration. In yet another implementation, the receiver 306 and the head assembly 201 are both configured in an interconnecting geometry comprising a T-slot (see FIGS. 3A and 3B). As shown in FIGS. 3A and 3B, in one implementation, the T-slot configuration of the receiver 306 can be comprised of a planar upper face 309, a planar lower face 307 and a planar medial face 308.

The receiver 306 can include two ends wherein a first end is open and second end is closed (not shown). Alternatively, both ends can be open or both ends can be closed (not shown).

As shown in FIGS. 2A-2C, in one implementation the one or more apertures 111, of the support member 202 include a first aperture 111*a* wherein an anchor assembly 301 is passable therethrough and lockably engagable with the support member 202. A second aperture 111*b* can be included wherein access is provided from the top portion 107 of the support member 202, through to the bottom portion 108 of the support member 202 (see FIGS. 2A-2C). As shown in FIGS. 2B and 2C, the second aperture 111*b* can also provide access to the head assembly 201 of the support 103 when the head assembly 201 is interconnected with the support member 202.

As shown in FIGS. 2A-2C, in one implementation the head assembly 201 is configured for interconnection with both the support member 202 and the base 102. The head assembly 201 includes a connector end 110, an aperture 111*c* and a locking means (for example, a flange) for securing the head assembly 201 to the support member 202. In one implementation the receiver 306 of the support member 202 and the head assembly 201 are configured in an interconnecting geometry comprising a T-slot. The interconnecting geometry between the head assembly 201 and the support member 202 can provide for adjustable positioning (and/or locking) of the support member 202 along the long axis of the head assembly 201 (see FIGS. 2B and 2C). As shown in FIG. 2B, the head assembly 201 can be contracted within the support member 202 to reduce the overall length of the screw assembly 101. In contrast, as shown in FIG. 2C, the head assembly 201 can be extended in relation to the support member 202 to increase the overall length of the screw assembly 101.

The connector end 110 of the head assembly 201 can be configured for interconnection of the support 103 and the base 102 of the screw assembly 101. In one implementation, the connector end 110 is configured for hinge-type interconnection of the support 103 and the base 102 of the screw assembly 101 (see FIGS. 2A-2E).

As shown in FIGS. 2A-2C, the aperture 111*c* of the head assembly can have a dimensional configuration to support a range of movement of the base 102 in relation to the support 103. Also as shown in FIGS. 2A-2C, the locking means for securing the head assembly 201 to the support member 202 can be comprised of a setscrew 104 disposed within the head assembly 201. In use, turning the setscrew 104 can result in contact between the setscrew 104 and the support member 202, thereby providing a means to secure the head assembly 201 to the support member 202. Alternatively, in another implementation, the locking means for securing the head assembly 201 to the support member 202 can be comprised of a cam.

A method of use of the invention for supporting a bony structure, can include the steps of: 1) delivering to bone a screw assembly 101 comprising a support 103 having a receiver 306, a base 102, an interconnection means 105, and a locking means; 2) deploying the support 103 substantially perpendicular to the long axis of the base 102; 3) passing through the support 103 and implanting one or more anchor assemblies 301 having a base 102 and a locking means into bone; 4) locking the bases 102 within one or more of the anchor assemblies 301; 5) locking one or more of the anchor assemblies 103 within the support 103 receiver 306; and 6) engaging the locking means of the screw assembly 101 to secure the position of the support 103 in relation to the base 102.

In a further implementation, the method of use described above can include disposing the support 103 adjacent to bone or adjacent to a spine. In one implementation, the method of use described above can include disposing the support 103 with the subcutaneous fat layer of the back. In another implementation, the method of use described above can include disposing the support 103 external to the body.

Another method of use of the invention for supporting a bony structure, can include the steps of: 1) delivering to bone a screw assembly 101 comprising: a support 103 comprising a support member 202 having a receiver 306, a head assembly 201 having a connector end 110 and an interconnection means 105; a base 102; an interconnection means 105, and a locking means; 2) deploying the support 102 substantially perpendicular to the long axis of the base 102; 3) passing through the support 103 and implanting one or more anchor assemblies 301 having a base 102 and a locking means into bone; 4) locking the bases 102 within one or more of the anchor assemblies 301; 5) locking one or more of the anchor assemblies 301 within the support 103 receiver 306; 6) locking the head assembly 201 within the support member 202; and 7) engaging the locking means of the screw assembly 101 to secure the position of the support 103 in relation to the base 102.

In one implementation, the method of use described above can include disposing the support 103 adjacent to bone or adjacent to a spine. In one implementation, the method of use described above can include disposing the support 103 with the subcutaneous fat layer of the back. In another implementation, the method of use described above can include disposing the support 103 external to the body.

A method of use of the invention for effecting a desired vertebral disk spacing, can include the steps of: 1) implanting a screw assembly 101 comprising a support 103 having a 306 receiver, a base 102, an interconnection means 105, and a locking means into a vertebra; 2) deploying the support 103 substantially perpendicular to the long axis of the base 102; 3) passing through the support 103 and implanting one or more anchor assemblies 301 having a base 102 and a locking means into a vertebra; 4) interconnecting the anchor assembly 301 with the receiver 306 of the support 103, wherein the anchor assembly 301 is unlocked within the receiver 306; 5) compressing or distracting the base 102 of the screw assembly 101 and the base 102 of the anchor assembly 301 in relation to each other (e.g. to achieve a parallel displacement of the instrumented vertebrae); 6) locking the anchor assembly 301 within the support 103 (e.g. using a setscrew 104 or cam); and 7) locking the support 103 position in relation to the base 102 using the screw assembly 101 locking means (e.g. using a setscrew 104 or cam).

The term "instrumented" as used herein defines a physical connection between a structure (e.g. a vertebra) and a medical device or instrument.

A method of use of the invention for effecting a desired curvature of the spine can include the steps of: implanting a screw assembly 101 comprising a support 103 having a receiver 306, a base 102, an interconnection means 105, and a locking means into a vertebra; 2) deploying the support 103 substantially perpendicular to the long axis of the base 102; 3) passing through the support 103 and implanting one or more anchor assemblies 301 having a base 102 and a locking means into a vertebra; 4) interconnecting the anchor assembly 301 with the receiver 306 of the support 103, wherein the anchor assembly 301 is unlocked within the receiver 306; 5) compressing or distracting the bases 102 in relation to each other (e.g. to affect the lordotic/kyphotic curvature of the spine); 6) locking the anchor assembly 301 within the support 103 (e.g. using a setscrew 104 or cam); and 7) locking the support 103 position in relation to the base 102 using the screw assembly 101 locking means (e.g. using a setscrew 104 or cam).

The method of supporting the spine can also be used in conjunction with a kyphoplasty procedure. Kyphoplasty is a percutaneous technique involving the use of an expandable structure, such as a balloon catheter, to create a cavity or void within the vertebral body, followed by filling the cavity with a bone substitute to form an "internal cast". The bone substitute could be any appropriate filling material used in orthopedic surgery, including, but not limited to, allograft or autograft tissue, hydroxyapatite, epoxy, PMMA bone cement or synthetic bone substitutes, medical grade plaster of Paris or calcium phosphate of calcium sulfate cements. Methods and instruments suitable for such treatment are more fully described in U.S. Pat. Nos. 4,969,888 and 5,108,404, which are incorporated herein by reference. Kyphoplasty can be used to reduce vertebral compression fractures and to move bone with precision, thus restoring as close to normal the pre-fracture anatomy of the vertebral body. Vertebral compression fractures caused by trauma (for example, due to automobile accidents or falls), have traditionally been treated with open reduction, internal fixation stabilization hardware, and fusion techniques using a posterior approach. The stabilization hardware is used to offload the fractured vertebral body and to stop motion across the disc so that bone graft can fuse one vertebra to the next and the stabilization hardware usually becomes a permanent implant. In trauma, the stabilization hardware may be designed to facilitate easy removal after fusion has occurred. Stabilization hardware can take many forms, including those described herein.

The combination of kyphoplasty and the insertion of stabilization hardware utilizing the naturally occurring interior muscle plane as described in Wiltse and Spencer, Spine (1988) 13(6):696-706, satisfies the goals of improving the quality of patient care through minimally invasive surgical therapy.

A number of preferred embodiments of the invention have been described. Nevertheless, it will be understood that various modifications may be made without departing from the spirit and scope of the invention. For example, while the some implementations have been described using screws to anchor into bony structures, the scope of the invention is not so limited. Any means of anchoring can be used, such as a cam, screw, staple, nail, pin, or hook. Accordingly, other embodiments are within the scope of the following claims.

What is claimed is:

1. A medical device for supporting a bony structure comprising:
   a base including an anchor extending along a long axis, the anchor being configured to penetrate the bony structure along the long axis,
   one or more anchor assemblies,
   a support configured for receiving said one or more anchor assemblies, the support including a top portion and a bottom portion, wherein the support includes one or more apertures extending through and opening at the top and bottom portions and a receiver between the top and bottom portions, and
   an interconnection means for coupling the base to the support, the interconnection means allowing the support to be positionable in a first position that is substantially parallel to the long axis of the anchor and secondarily positionable substantially perpendicular to the long axis of the anchor,
   the base and the one or more anchor assemblies configured for attachment to the structure in a patient, wherein the one or more anchor assemblies extend into the receiver from the bottom portion of the support when the support is positioned substantially perpendicular to the long axis of the anchor, the one or more anchor assemblies being deformable through the one or more apertures from the top portion of the support to engage and lock the one or more anchor assemblies to the receiver.

2. The medical device of claim 1, wherein the structure supported is bone selected from the group consisting of a vertebra, femur, tibia, fibula, humerus, radius, ulna, calcaneous, and a pelvis.

3. The medical device of claim 1, wherein the support has an overall length sized for subcutaneous support of the posterior of a spine.

4. The medical device of claim 1, wherein the base comprises:
   a base head having a shape and a locking means and the anchor extends from the base head along the long axis.

5. The medical device of claim 4, wherein the base head shape is an open saddle-type head and the interconnection means includes a connector end extending through the open saddle-type head and an aperture adjacent the connector end having a dimensional configuration to receive a portion of the saddle-type head therethrough when the support is positioned substantially perpendicular to the long axis of the anchor.

6. The medical device of claim 4, wherein the locking means comprises a setscrew,
   wherein the setscrew is configured to link the support and the base, and
   wherein tightening the setscrew effects locking of the support in a position relative to a long axis of the base.

7. The medical device of claim 4, wherein the anchor is selected from the group consisting of a screw, staple, nail, hook and a pin.

8. The medical device of claim 4, wherein the anchor is a screw configured for insertion into the pedicle of a vertebra.

9. The medical device of claim 1, wherein the support has a shape selected from the group consisting of a board, plate, elongated cross-section, oval, square, I-beam and a rod.

10. The medical device of claim 1, wherein the interconnection means includes a connector end that is configured for interconnection of the support and the base.

11. The medical device of claim 1, wherein the interconnection means includes a connector end that is configured for hinge-type interconnection of the support and the base.

12. The medical device of claim 1, wherein the interconnection means includes a first connector end proximal aperture having a dimensional configuration to support a range of movement of the base in relation to the support, and, the one or more apertures of the support includes at least one aperture providing access to means for locking the anchor assembly to the support, when assembled with the support.

13. The medical device of claim 1, wherein the interconnection means includes a head assembly with a connector end for engagement with a head of the base.

14. The medical device of claim 13, wherein the one or more apertures include
   a first aperture wherein the anchor assembly is passable therethrough and lockably engagable with the support member, and
   a second aperture wherein access is provided from the top portion of the support member to access the head assembly.

15. The medical device of claim 13, wherein the head assembly comprises:
   an aperture adjacent the connector end having a dimensional configuration supporting a range of movement of the base in relation to the support when the connector end is positioned in the head of the base, and
   a locking means for securing the head assembly to the support member, wherein the head assembly is configured for movement along the support member to adjust a length of the support member extending from the head assembly and the locking means secures the head assembly and the support member at the length.

16. The medical device of claim 1, wherein:
   the base includes a head and the anchor extends from the head,
   the support member extends between the one or more anchor assemblies and the base, wherein the one or more apertures includes first and second apertures extending through and opening at top and bottom portions of the support, wherein the first aperture receives at least one of the anchor assemblies and a locking assembly to lock the at least one anchor assembly to the support member;
   the interconnection means comprises a head assembly movably coupled with one end of the support member, the head assembly including a connector end and a third aperture between the connector end and the support member, wherein the head of the base receives the connector end so that the third aperture and support member are movable relative to the base from the first position to be secondarily positionable where the head assembly and the support member extend substantially perpendicular to the long axis of the anchor and at least a portion of the base head is positioned in the third aperture in the second position, wherein the head assembly includes a locking means movable in the receiver in alignment with the second aperture and the locking means is deformable through the opening of the second aperture at the top portion of the support to engage the locking means to the receiver; and
   further comprising a locking member for securing the connector end to the head of the base.

17. A medical device for supporting a bony structure in a patient, comprising:
   a base including a head and an anchor extending from the head for engaging the bony structure, wherein the anchor extends along a long axis and is configured to penetrate the bony structure along the long axis,
   at least one anchor assembly for engaging the bony structure,
   a support member extending between the anchor assembly and the base, wherein the support includes first and second apertures extending through and opening at top and bottom portions of the support and a receiver between the top and bottom portions, wherein the first aperture receives a locking assembly to lock the anchor assembly to the support member;
   a head assembly movably coupled with one end of the support member, the head assembly including a connector end and a third aperture between the connector end and the support member, wherein the base head receives the connector end so that the third aperture and support member are movable relative to the base from a first position where the head assembly and support member extend substantially parallel with the long axis of the anchor to a second position where the head assembly and the support member extend substantially perpendicular to the long axis of the anchor and at least a portion of the base head is positioned in the third aperture in the second position, wherein the head assembly includes a locking means movable in the receiver in alignment with the second aperture and the locking means is deformable through the opening of the second aperture at the top portion of the support to engage the locking means to the receiver; and
   a locking member for securing the connector end to the head of the base.

18. The medical device of claim 17, wherein the head assembly is configured for movement along the support member to adjust a length of the support member extending from the head assembly and wherein the locking means secures the head assembly and the support member at the length.

19. The medical device of claim 17, wherein when the support is positioned substantially perpendicular to the long axis of the base the at least one anchor assembly is positionable to extend from the bony structure into the receiver from the bottom portion of the support, the at least one anchor assembly being deformable through the first aperture from the top portion of the support to engage and lock the at least one anchor assembly to the receiver.

20. The medical device of claim 17, wherein the base head is an open saddle-type head and the connector end extends through the open saddle-type head and the third aperture includes a dimensional configuration to receive a portion of the saddle-type head therethrough when the support is positioned substantially perpendicular to the long axis of the anchor.

* * * * *